United States Patent
Singh et al.

(10) Patent No.: US 10,840,553 B2
(45) Date of Patent: Nov. 17, 2020

(54) FREE-SOLVENT-FREE LITHIUM SULFONAMIDE SALT COMPOSITIONS THAT ARE LIQUID AT ROOM TEMPERATURE, AND USES THEREOF IN LITHIUM ION BATTERY

(71) Applicant: SES Holdings Pte. Ltd., Singapore (SG)

(72) Inventors: Rajendra P. Singh, Woburn, MA (US); Shubha Nageswaran, Billerica, MA (US); Qichao Hu, Arlington, MA (US)

(73) Assignee: SES Holdings Pte. Ltd., Singapore (SG)

( * ) Notice: Subject to any disclaimer, the term of this patent is extended or adjusted under 35 U.S.C. 154(b) by 0 days.

(21) Appl. No.: 16/530,683

(22) Filed: Aug. 2, 2019

(65) Prior Publication Data
US 2020/0280098 A1    Sep. 3, 2020

Related U.S. Application Data

(60) Provisional application No. 62/812,446, filed on Mar. 1, 2019, provisional application No. 62/830,601, filed on Apr. 8, 2019.

(51) Int. Cl.
*H01M 10/0568* (2010.01)
*H01M 10/0569* (2010.01)
(Continued)

(52) U.S. Cl.
CPC ....... *H01M 10/0568* (2013.01); *C07C 311/10* (2013.01); *H01G 11/62* (2013.01);
(Continued)

(58) Field of Classification Search
None
See application file for complete search history.

(56) References Cited

U.S. PATENT DOCUMENTS 9,960,451 B1   5/2018  Zhamu et al.
10,319,989 B2 *  6/2019  Chen .................. H01M 4/136
(Continued)

FOREIGN PATENT DOCUMENTS

EP   3323792 A1   5/2018

OTHER PUBLICATIONS

Miao, Rongrong et al., A new ether-based electrolyte for dendrite-free lithium-metal based rechargeable batteries; Scientific Reports; Feb. 16, 2016; www.nature.com/scientificreports; 6:21771; DOI:10.1038/srep21771; pp. 1-9.

(Continued)

*Primary Examiner* — Joseph D Anthony
(74) *Attorney, Agent, or Firm* — Downs Rachlin Martin PLLC

(57) ABSTRACT

Free-solvent-free lithium sulfonimide salt compositions that are liquid at room temperature, and methods of making free-solvent-free liquid lithium sulfonimide salt compositions. In an embodiment, the methods include mixing one or more lithium sulfonimide salts with one or more ether-based solvents and then removing the free solvent(s) under suitable vacuum, temperature, and time conditions so as to obtain a free-solvent-free liquid lithium sulfonimide salt composition that is liquid at room temperature. In an embodiment, the only solvent molecules that remain in the liquid lithium sulfonimide salt composition are adducted with lithium sulfonimide salt molecules. An example automated processing system for making free-solvent-free liquid lithium sulfonimide salts is also disclosed.

30 Claims, 2 Drawing Sheets

(51) Int. Cl.
*H01M 10/0525* (2010.01)
*H01G 11/62* (2013.01)
*C07C 311/10* (2006.01)

(52) U.S. Cl.
CPC ... *H01M 10/0525* (2013.01); *H01M 10/0569* (2013.01); *H01M 2300/0025* (2013.01)

(56) References Cited

U.S. PATENT DOCUMENTS

| | | | | |
|---|---|---|---|---|
| 10,347,904 B2* | 7/2019 | Cho | | H01M 4/134 |
| 10,615,457 B2* | 4/2020 | Hwang | | H01M 4/382 |
| 2006/0194115 A1* | 8/2006 | De Jonghe | | H01M 4/366 |
| | | | | 429/246 |
| 2011/0179636 A1* | 7/2011 | De Jonghe | | H01M 4/581 |
| | | | | 29/623.1 |
| 2015/0357637 A1* | 12/2015 | Yamanoi | | H01M 32/30 |
| | | | | 429/231.8 |
| 2016/0149262 A1 | 5/2016 | Singh | | |
| 2016/0233549 A1* | 8/2016 | Tiruvannamalai | | |
| | | | | H01M 10/0569 |
| 2016/0248122 A1* | 8/2016 | Hwang | | H01M 10/052 |
| 2016/0293943 A1* | 10/2016 | Hu | | H01M 4/1395 |
| 2016/0372743 A1* | 12/2016 | Cho | | H01M 4/62 |
| 2018/0183122 A1* | 6/2018 | Grey | | H01M 4/90 |
| 2018/0190973 A1* | 7/2018 | Chen | | H01M 10/052 |
| 2018/0370799 A1 | 12/2018 | Lim | | |
| 2020/0155964 A1* | 5/2020 | Singh | | C01B 21/086 |

OTHER PUBLICATIONS

Forero-Saboya, Juan et al., Solvent-free lithium and sodium containing electrolytes based on pseudo-delocalized anions; Royal Society of Chemistry; https://pubs.rsc.org/en/content/articlehtml/2019/cc/c8cc07076h; DOI: 10.1039/C8CC07076H (Communication) Chem. Commun., 2019, 55, 632-635; Dec. 10, 2018.

* cited by examiner

US 10,840,553 B2

FREE-SOLVENT-FREE LITHIUM SULFONAMIDE SALT COMPOSITIONS THAT ARE LIQUID AT ROOM TEMPERATURE, AND USES THEREOF IN LITHIUM ION BATTERY

RELATED APPLICATION DATA

This application claims the benefit of priority of U.S. Provisional Patent Application Ser. No. 62/812,446, filed Mar. 1, 2019, and titled "LIQUID LITHIUM SALT: FREE-SOLVENT-FREE LITHIUM ELECTROLYTE WITH >12 MOLAR CONCENTRATION IN ETHER-BASED SOLVENTS" and of U.S. Provisional Patent Application Ser. No. 62/830,601, filed Apr. 8, 2019, and titled "LIQUID LITHIUM SALT: FREE-SOLVENT-FREE LIQUID LITHIUM BIS(FLUOROSULFONYL)IMIDE", each of which is incorporated by reference herein in its entirety.

FIELD OF THE INVENTION

The present invention generally relates to the field of lithium sulfonimide salts. In particular, the present invention is directed to free-solvent-free lithium sulfonimide salt compositions that are liquid at room temperature, and uses thereof.

BACKGROUND

There is no lithium salt today that is liquid at room temperature (i.e., ~20° C. to ~25° C.). The only way one can get a room-temperature liquid containing a lithium salt is by dissolving the lithium salt in solvent to yield a solution. Removing the solvent from the room-temperature solution via conventional means simply yields-back solid lithium salt. A simple example in this category is the dissolving of solid lithium chloride in water to get a room-temperature solution. Removing the water from the room-temperature solution yields-back the lithium chloride as a solid.

Lithium salts have been used in electrolytes for, for example, lithium-ion batteries and supercapacitors. There is a variety of lithium salts available today, such as lithium bis(fluoro-sulfonyl)imide (LiFSI), lithium bis(trifluoromethanesulfonyl)imide (LiTFSI), and lithium fluoro-sulfonyl(trifluoromethanesulfonyl)imide (LiFTFSI). However, they are all solid at room temperature. Ionic liquids have also been reported that can dissolve the solid lithium salts to yield liquid electrolytes, but the concentration of the lithium salts is not very high (generally less than 3 molar). Free-solvent-free lithium salts that are liquid at room temperature would be desirable for a variety of applications, including lithium-based batteries, especially secondary lithium-based batteries, and supercapacitors, among other things. For example, a liquid, i.e., a free-solvent-free, lithium salt could be used directly as an electrolyte without the need for any solvent. Solvents for lithium-based electrolytes are flammable, so avoiding solvents reduces the possibility of fire and/or explosions. In addition, a neat liquid lithium salt has a very high concentration of lithium ions available for flow of electrical energy within the electrolyte.

SUMMARY OF THE DISCLOSURE

In an implementation, the present disclosure is directed to a method of synthesizing a free-solvent-free lithium sulfonimide salt composition. The method includes contacting at least one anhydrous lithium sulfonimide salt with at least one anhydrous ether-based solvent under inert conditions to create the solution containing the at least one anhydrous lithium sulfonimide salt, wherein the at least one anhydrous ether-based solvent in the solution comprises a free portion that is not adducted to the at least one anhydrous lithium sulfonimide salt; and removing substantially all of the free portion of the at least one ether-based solvent in the solution so that the free-solvent-free lithium sulfonimide salt composition remains, wherein the free-solvent-free lithium sulfonimide salt composition is liquid at room temperature.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
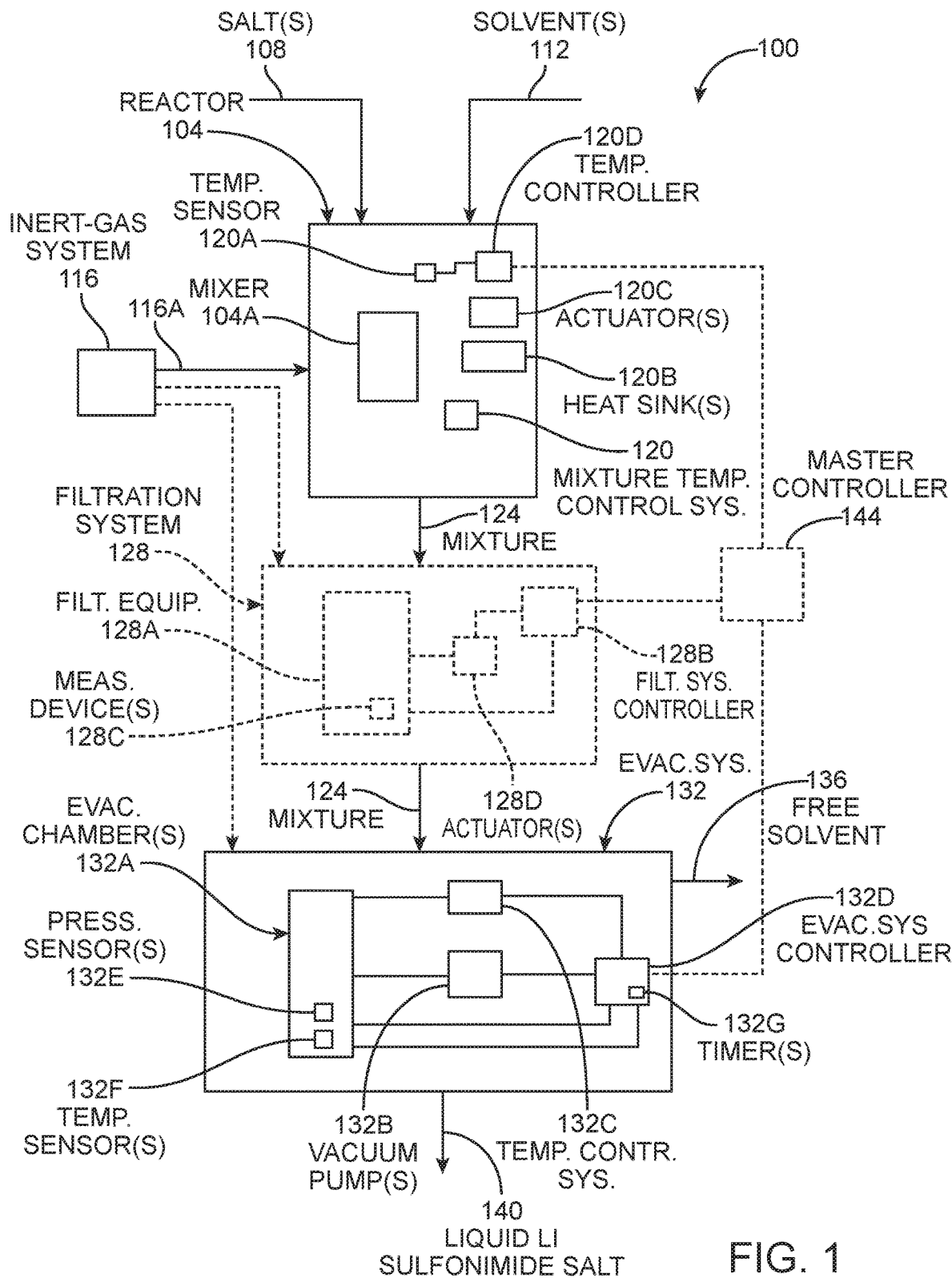
FIG. 1 is a diagram illustrating an example automated processing system for making a free-solvent-free liquid lithium sulfonimide salt composition of the present disclosure.

In some aspects, the present disclosure is directed to methods of synthesizing lithium sulfonimide salt compositions that are liquid at room temperature and are substantially or completely free of free solvents. Such liquid lithium sulfonimide salt compositions are referred to herein as "free-solvent-free", which is a state that typically occurs after exposing the compositions to certain temperatures and certain vacuums for periods of time wherein there is no further reduction in solvents but the composition remains liquid. As used herein and in the appended claims, "room temperature" is taken to be 25° C., though it can extend lower, such as to 20° C. As described and exemplified below in detail, in some embodiments, these lithium sulfonimide salt compositions are made using at least one anhydrous ether-based solvent to make a solution from a lithium sulfonimide salt or a combination of two or more lithium sulfonimide salts, such as, for example, a combination of lithium bis(fluoro-sulfonyl)imide (LiFSI) and lithium bis(trifluoromethanesulfonyl)imide (LiTFSI) or other lithium fluorinated and/or perfluorinated sulfonimide salt. Ether-based solvents have been found to have strong coordination with the lithium sulfonimide salt compositions, unlike other solvents. The free portion of the at least one anhydrous ether-based solvent is then removed, either entirely or to an extent practicable under available processing conditions, from the solution to yield a composition that consists essentially of an adduct of molecules of the lithium sulfonimide salt(s) and molecules of the at least one anhydrous ether-based solvent used to make the solution.

In some embodiments, the lithium sulfonimide salt compositions may be synthesized by mixing a lithium base with a fluorine-containing acid in at least one anhydrous ether-based solvent to not only synthesize the lithium sulfonimide salt but to also create a solution from which all or substantially all of the at least one anhydrous ether-based solvent is removed to create the lithium sulfonimide salt composition. As in the previous embodiment, the lithium sulfonimide salt composition consists essentially of an adduct of molecules of the lithium sulfonimide salt with molecules of the at least one anhydrous ether-based solvent. In both of the foregoing embodiments, the resulting lithium sulfonimide salt compositions are referred to herein and in the appended claims as "free-solvent-free" to denote the fact that they are not solutions because they lack or substantially lack free solvent molecules.

It is noted that the use of "free-solvent-free" relative to lithium sulfonimide salt compositions disclosed herein shall include such compositions that are completely free of all free, i.e., non-adducted, molecules of the anhydrous ether-based solvent(s) used in making the compositions as well as such compositions that are substantially free of free, i.e., non-adducted, molecules of the anhydrous ether-based solvent(s) used in making the compositions. In this context, "substantially" means that as much as possible or practicable of the anhydrous ether-based solvent(s) used in making the compositions has/have been removed such that the lithium sulfonimide salt composition at issue consists essentially of the corresponding salt+solvent adduct. In some embodiments, "free-solvent-free" means that the corresponding lithium sulfonimide salt composition has less than about 0.5% by weight of solvent. In some embodiments, "free-solvent-free" means that the corresponding lithium sulfonimide salt composition has less than about 0.3% by weight of solvent. In some embodiments, "free-solvent-free" means that the corresponding lithium sulfonimide salt composition has less than about 0.1% by weight of solvent. In some embodiments, "free-solvent-free" means the lithium sulfonimide salt composition that remains when in-vacuo solvent-removal conditions (i.e., pressure and temperature) are continued and the weight of the lithium sulfonimide salt composition no longer continues to reduce. This is an indication that all or substantially all of the free solvent(s) is/are removed.

In this connection, as used herein and in the appended claims, the term "consisting essentially of" means that the matter so referred to is composed of that matter plus any impurity(ies) that may be present by virtue of synthesis, hygroscopic affinity, or otherwise, and/or any other material that is not intentionally present in the matter.

As additionally used herein and in the appended claims, the term "anhydrous" refers to having about 1% by weight of water or less, typically about 0.5% by weight of water or less, often about 0.1% by weight of water or less, more often about 0.01% by weight of water or less, and most often about 0.001% by weight of water or less. Within this definition, the term "substantially anhydrous" refers to having about 0.1% by weight of water or less, typically about 0.01% by weight of water or less, and often about 0.001% by weight of water or less.

Throughout the present disclosure and the appended claims, the term "about" when used with a corresponding numeric value refers to ±20% of the numeric value, typically ±10% of the numeric value, often ±5% of the numeric value, and most often ±2% of the numeric value. In some embodiments, the term "about" can be taken as being the actual numerical value.

When describing a chemical reaction, such as any of the synthesis and purification reactions described herein and/or addressed in the appended claims, the terms "treating", "contacting", and "reacting", are used interchangeably and refer to adding or mixing two or more reagents under the conditions sufficient to produce the indicated and/or desired product(s). It should be appreciated that the reaction that produces the indicated and/or desired product may not necessarily result directly from the combination of the reagent(s) that was/were initially added. That is, there may be one or more intermediates that are produced in the mixture and ultimately lead to the formation of the indicated and/or desired product.

In another aspect, the present disclosure is directed to uses of lithium sulfonimide salt compositions of the present disclosure. For example, lithium sulfonimide salt compositions of the present disclosure can be used as molten salts to make electrolytes that can be used in any suitable electrochemical device, such as a battery or supercapacitor.

Details of the foregoing and other aspects of the present disclosure are described below.

Example Methods of Synthesizing Room-Temperature Lithium Sulfonimide Salt Compositions In some embodiments, a free-solvent-free lithium sulfonimide salt composition that is liquid at room temperature (20° C. in this disclosure and appended claims) can be synthesized as follows. First, a solution containing an anhydrous lithium sulfonimide salt and at least one anhydrous ether-based solvent may be provided. Examples of lithium sulfonimide salt compositions that can be used for the anhydrous lithium sulfonimide salt include, but are not necessarily limited to, LiFSI, LiTFSI, and lithium fluorosulfonyl(trifluoromethylsulfonyl)-imide (LiFTFSI). Examples of anhydrous ether-based solvents that can be used for the one or more anhydrous ether-based solvents include, but are not necessarily limited to, dimethoxyethane, ethoxymethoxyethane, diethoxyethane, dimethoxymethane, diethoxymethane, ethoxymethoxymethane, dioxane, and crown ethers, among others. Generally, any ether-based solvent can be used.

In some instantiations, providing the solution may include making the solution starting with a lithium sulfonimide salt. In an example, making the solution includes providing a lithium sulfonimide salt in solid form and contacting the solid lithium sulfonimide salt with at least one anhydrous ether-based solvent. In an example, the amount of the at least one anhydrous ether-based solvent used is the minimum amount, or about the minimum amount, needed to create the solution. By "minimum amount" in the context of the at least one anhydrous ether-based solvent, it is meant that the at least one anhydrous ether-based solvent is provided in an amount substantially at which the solid lithium sulfonimide salt no longer continues to dissolve. In some embodiments, the minimum amount of the at least one anhydrous ether-based solvent is about 20 wt. % of the solution.

The contacting of the lithium sulfonimide salt with the at least one anhydrous ether-based solvent may be performed in a dry inert atmosphere, such as in a dry inert gas, such as argon and/or nitrogen gas, among others. The contacting of the lithium sulfonimide salt with the at least one anhydrous ether-based solvent may be performed in any suitable manner, such as portion-wise, by predetermined amount (e.g., if proportions leading to the minimum amount have been predetermined), among others. The process of making the solution that starts with a lithium sulfonimide salt may be performed at or near room temperature, such as in a range of about 15° C. to about 30° C. However, this process may be performed at another suitable temperature at which a liquid solution may be obtained. The process of making the solution may be assisted by stirring, for example, using any suitable stirring device. In some instantiations, stirring is performed continuously for at least about 10 minutes during and/or after the contacting of the lithium sulfonimide salt with the at least one anhydrous ether-based solvent.

In some instantiations, providing the solution may include making the solution as part of synthesizing a lithium sulfonimide salt. In an example, the making of the solution may include reacting a lithium base with a fluorine-containing acid in the at least one anhydrous ether-based solvent under conditions sufficient to neutralize the solution and form the lithium sulfonimide salt in the solution. In an example, the lithium base may be selected from a group that includes, but is not necessarily limited to, lithium carbonate and lithium hydroxide, and the fluorine-containing acid may be selected from a group that includes, but is not necessarily limited to, $FSO_2NHSO_2F$ (HFSI) and $CF_3SO_2NHSO_2F$ (HFTFSI). In some instantiations, the synthesis of the lithium sulfonimide salt may result in impurities that precipitate within the solution. If so, the solution may be filtered, for example, using any suitable filtering technique known in the art, to remove such impurities to create a clear, colorless liquid filtrate. The process of making the solution along with synthesizing a lithium sulfonimide salt may be performed at or near room temperature, such as in a range of about 15° C. to about 30° C. However, this process may be performed at another suitable temperature at which a liquid solution may be obtained. The process of making the solution may be assisted by stirring, for example, using any suitable stirring device. In some instantiations, stirring is performed continuously for at least about 10 minutes during and/or after the contacting of the lithium sulfonimide salt with the at least one anhydrous ether-based solvent.

Whichever way the solution containing an anhydrous lithium sulfonimide salt and at least one anhydrous ether-based solvent is provided, such as any of the ways described above, all or substantially all of the free, i.e., non-adducted, portion of the at least one anhydrous either-based solvent is removed from the solution so as to obtain the free-solvent-free liquid lithium sulfonimide salt composition. As mentioned above, the free-solvent-free liquid lithium sulfonimide salt composition consists essentially of an adduct composed of molecules of the lithium sulfonimide salt and molecules of the at least one anhydrous ether-based solvent. The removal of the free portion of the at least one anhydrous ether-based solvent may be performed in any suitable manner.

For example, the free portion of the at least one anhydrous ether-based solvent can be removed from the solution in vacuo, such as at a pressure of about 100 Torr or less, 10 Torr or less, 1 Torr or less, 0.1 Torr or less, or 0.01 Torr or less, among others. While subjected to the vacuum, the solution may be at a temperature within a range of about −78° C. to about 100° C., a range of about 20° C. to about 70° C., a range of about 0° C. to about 35° C., among others. In some embodiments, such as embodiments using any combination of pressure and temperature in the ranges just mentioned, it can take 48 hours or more to obtain the free-solvent-free lithium sulfonimide salt. Following removal of the free portion of the at least one anhydrous ether-based solvent, the resulting free-solvent-free lithium sulfonimide salt composition is a clear, colorless product that is liquid at room temperature. In one example, free solvents were removed by evacuating to less than 0.01 Torr at a temperature in a range of about 0° C. to about 35° C. to achieve a constant weight liquid product. By "constant weight" it is meant that the removal process reached a point that the weight of the liquid lithium sulfonimide salt composition no longer reduced. This indicates that any remaining solvent is fully coordinated with the lithium sulfonimide salt to provide a free-solvent-free liquid lithium sulfonimide salt composition that is a single composition.

As noted above, the free-solvent-free liquid lithium sulfonimide salt composition consists essentially of an adduct of molecules of the lithium sulfonimide salt and molecules of the at least one anhydrous ether-based solvent. While it can be desired that water not be present in the free-solvent-free liquid lithium sulfonimide salt composition, in practice it is difficult to remove all water. Consequently, in some embodiments, it is desirable that the free-solvent-free liquid lithium sulfonimide salt composition have a water content of about 2,000 parts-per-million (ppm) or less, about 1,000 ppm or less, about 500 ppm or less, about 200 ppm or less, about 100 ppm or less, or about 2 ppm or less, among others.

Methods of synthesizing free-solvent-free liquid lithium sulfonimide salt composition of the present disclosure may be adapted to batch processing and continuous processing. Referring now to the drawings, FIG. 1 illustrates an example automated processing system 100, which can be desirable for making free-solvent-free liquid lithium sulfonimide salt compositions in commercial-scale amounts. In the example of FIG. 1, automated processing system 100 includes a reactor 104 that is continuously or continually fed with one or more lithium sulfonimide salts (indicated in FIG. 1 by arrow 108) and one or more ether-based solvents (indicated in FIG. 1 by arrow 112). Not illustrated, but which those skilled in the art will understand may be present, are one or more devices for feeding the one or more lithium sulfonimide salts 108 into the reactor 104 in accurate amounts (e.g., weights) and one or more devices for feeding the one or more ether-based solvents 112 into the reactor 104 in accurate amounts (e.g., weights). The optimal amounts of each of the lithium sulfonimide salt(s) 108 and the ether-based solvent(s) 112 may be determined using any suitable methodologies, such as experimentation and/or computer modeling using suitable process parameters, which may themselves be determined using any suitable methodologies.

The reactor 104 may include a mixer 104A and corresponding control system (not shown) for properly mixing together the lithium sulfonimide salt(s) 108 and the ether-based solvent(s) 112. As mentioned above, the lithium sulfonimide salt(s) 108 and the ether-based solvent(s) 112 should each be in an anhydrous state. Consequently, the reactor 104 and other components of automated processing system 100 provide an inert environment for the corresponding processes. Such an inert environment may be provided by an inert-gas system 116, including any necessary controller (not shown), that uses one or more inert gases (indicated in FIG. 1 by arrow 116A), such as argon and nitrogen.

Because the mixing of the lithium sulfonimide salt(s) 108 and the ether-based solvent(s) 112 is exothermic and it is desired to keep the mixing isothermal, in this example the reactor 104 is provided with a mixture-temperature control system 120 that monitors the temperature of the mixture within the reactor 104. While the mixture within the reactor 104 is not shown, the mixture is illustrated exiting the reactor 104, as indicated by arrow 124. As those skilled in the art will appreciate, the mixture-temperature control system 120 may include: one or more thermal probes and/or other temperature sensors 120A for measuring the temperature of the mixture 124 within the reactor 104; one or more heat sinks 120B, such as one or more heat exchangers; one or more actuators 120C for controlling the amount of heat the heat sink(s) 120B remove from the mixture 124, and a temperature controller 120D for controlling the actuator(s) 120C as a function of the temperature of the mixture 124. The reactor 104 may include one or more controllers (not shown) for controlling any other operation of the reactor 104, such as releasing of the mixture 124, among others.

If the mixture 124 contains insoluble impurities, automated processing system 100 may optionally include a filtration system 128 for filtering such impurities from the mixture 124. The filtration system 128 may include any suitable filtration equipment 128A, such as porous filters having a pore size in a range of about 50 microns to about 200 microns, among others. The filtration system 128 may be fluidly connected to the inert-gas system 116 as needed to ensure that the mixture 124 remains in an inert environment during filtration. In other embodiments where filtration needs inert gas, an inert-gas system different from inert-gas system 116 may be used. The filtration system 128 may include any necessary filtration controller 128B and corresponding measurement device(s) 128C and actuator(s) 128D, etc., needed for controlling the filtration that the filtration system 128 performs.

The automated processing system 100 includes an evacuation system 132 for controllably removing the free solvent (illustrated by arrow 136 exiting from the evacuation system 132) from the mixture 124 so as to create the desired free-solvent-free liquid lithium sulfonimide salt 140. The evacuation system 132 may include one or more vacuum chambers 132A and one or more vacuum pumps 132B for providing the vacuum chamber(s) 132A with the desired amount of vacuum. Example vacuum pressures for the solvent removal process are described above. The evacuation system 132 may also include one or more temperature control systems 132C for controlling the temperature within the vacuum chamber(s) 132A. Example temperatures for the solvent removal process are described above. The evacuation system 132 may also include one or more evacuation-system controllers 132D for controlling all aspects of the solvent-removal process performed by the evacuation system 132. For example, the evacuation-system controller(s) 132D may use feedback control to control the vacuum level(s) within the vacuum chamber(s) 132A, for example, using one or more suitable pressure sensors 132E. The evacuation-system controller(s) 132D may use feedback control to control the temperature(s) within the vacuum chamber(s) 132A, for example, using one or more suitable temperature sensors 132F. The evacuation-system controller(s) 132D may also include one or more timers 132G that control the amount of time that the mixture 124 within the vacuum chamber(s) 132A is subjected to the desired vacuum level(s) and temperature(s). The evacuation system 132 may also include actuators, conveyors, and/or other components (not shown) for moving the mixture 124 and/or the products and byproducts into, through, and/or out of the evacuation system 132. The evacuation-system controller(s) 132D may include suitable machine-executable instructions for performing these and any other pertinent function(s) to make the automated processing system 100 fully functional and fully automated.

In some embodiments, automated processing system 100 may include a master controller 144 that communicates with each of the controllers 120D, 128B, and 132D and any other controllers, actuator, sensors, feed devices, etc., to control the overall operation of the automated processing system 100. In some embodiments, master controller 144 may perform all of the functions of controllers 120D, 128B, and 132D. As those skilled in the art will readily appreciate, each controller 120D, 128B, 132D, 144, and any controller not illustrated, if any, may be any suitable controller, such as a microprocessor-based controller that includes hardware memory containing suitable machine-executable instructions for performing the necessary/desired functions, and one or more microprocessors in operative communication with the hardware memory so as to be able to process such machine-executable instructions. Examples of controllers that can be used as any one of the controllers 120D, 128B, 132D, 144, and any controller not illustrated, if any, include, but are not limited to, systems on chip, personal computers, mainframe computers, and programmable logic controllers, among others. Fundamentally, there is no limitation on the type of machine used for each of the controllers 120D, 128B, 132D, 144, and any controller not illustrated, if any. Those skilled in the art will readily understand how to implement all aspects of the automated processing system 100 with a full understanding of the methodologies disclosed herein for making free-solvent-free liquid lithium sulfonimide salt.

EXPERIMENTAL EXAMPLES

Unless otherwise stated, all chemicals used in the following examples were of high purity and obtained from commercial sources. Stringent precautions were taken to exclude the moisture in the processes, and reactions were performed in well-ventilated hoods.

Example 1

Room-temperature liquid lithium sulfonimide salt composition using LiFSI and dimethoxyethane: In a 250 mL round-bottom dry flask, solid LiFSI (112 g) was taken under an argon atmosphere. The flask was equipped with a stirring bar and cooled with an ice bath. Anhydrous dimethoxyethane (65 g) was added into the flask portion-wise to dissolve the LiFSI. After complete addition of dimethoxyethane, the ice bath was removed, and the solution stirred at room temperature for 10 minutes using the stirring bar. The obtained liquid solution was evacuated in a vacuum <0.01 Torr at 35° C. for 24 hours to get 152 g of liquid LiFSI salt composition, the appearance of which was of a clear colorless liquid. The conductivity was 2.48 m/S/cm.

Example 2

Room-temperature liquid lithium sulfonimide salt composition using LiFSI and dimethoxyethane: In a 250 mL round-bottom dry flask, solid LiFSI (134.64 g) was taken under an argon atmosphere. The flask was equipped with a stirring bar and cooled with an ice bath. Anhydrous dimethoxyethane (40 g) was added into the flask portion-wise to dissolve the LiFSI. After complete addition of dimethoxyethane, the ice bath was removed, and the solution stirred at room temperature for 10 minutes using the stirring bar. The obtained liquid solution was evacuated in a vacuum <0.01 Torr at 35° C. for 24 hours to get 174.6 g of liquid LiFSI salt composition.

Example 3

Room-temperature liquid lithium sulfonimide salt composition using LiFSI and dimethoxyethane: In a 250 mL round-bottom dry flask, solid LiFSI (33.1 g) was taken under an argon atmosphere. The flask was equipped with a stirring bar and cooled with an ice bath. Anhydrous dimethoxyethane (13.5 g) was added into the flask portion-wise to dissolve the LiFSI. After complete addition of the dimethoxyethane, the ice bath was removed, and the solution was stirred at room temperature for 10 minutes using the stirring bar. The obtained liquid solution was evacuated in a vacuum <0.01 Torr at 35° C. for 24 hours to get 45 g of liquid LiFSI salt composition.

Example 4

Room-temperature liquid lithium sulfonimide salt composition using LiFTFSI and dimethoxyethane: In a 250 mL round-bottom dry flask, solid LiFTFSI (42 g) was taken under an argon atmosphere. The flask was equipped with a stirring bar and cooled with an ice bath. Anhydrous dimethoxyethane (40 g) was added into the flask portion-wise to dissolve the LiFTFSI. After complete addition of the dimethoxyethane, the ice bath was removed, and the reaction mixture stirred at room temperature for 10 minutes using the stirring bar. The obtained liquid solution was evacuated in a vacuum <0.01 Torr at 35° C. for 48 hours to get 54 g of liquid LiFTFSI salt composition.

Example 5

Room-temperature liquid lithium sulfonimide salt composition using LiFSI and diethoxymethane: In a 250 mL round-bottom dry flask, solid LiFSI (80 g) was taken under an argon atmosphere. The flask was equipped with a stirring bar and cooled with an ice bath. Anhydrous diethoxymethane (40 g) was added into the flask portion-wise to dissolve the LiFSI. After complete addition of the dimethoxyethane, the ice bath was removed, and the reaction mixture stirred at room temperature for 10 minutes using the stirring bar. The obtained liquid solution was evacuated in a vacuum <0.01 Torr at 35° C. to get 109 g of liquid LiFSI salt composition, the appearance of which was of a clear colorless liquid.

Example 6

Room-temperature liquid lithium sulfonimide salt composition using LiFSI and diethoxyethane: In a 250 mL round-bottom dry flask, solid LiFSI (33.1 g) was taken under an argon atmosphere. The flask was equipped with a stirring bar and cooled with an ice bath. Anhydrous diethoxyethane (20 g) was added into the flask portion-wise to dissolve the LiFSI. After complete addition of the dimethoxyethane, the ice bath was removed, and the reaction mixture stirred at room temperature for 10 minutes using the stirring bar. The content of the flask was evacuated in a vacuum <0.01 Torr at 35° C. for 48 hours to get 46 g of liquid LiFSI salt composition.

Example 7

Room-temperature liquid lithium sulfonimide salt composition using lithium carbonate, HFSI, and dimethoxyethane: In a 250 mL dry flask, lithium carbonate (14.4 g) is suspended in 50 g of anhydrous dimethoxyethane. The suspension was cooled with an ice bath. HFSI (72.4 g) was added dropwise, as neat with stirring. Following the complete addition of the HFSI, the ice bath was removed, and the solution was stirred at room temperature for 1 hour. The insoluble impurities were removed by filtration. The filtrate was evacuated in a vacuum <0.01 Torr at 35° C. for 48 hours to get 99.0 g of liquid lithium LiFSI salt composition.

Example Uses of Room-Temperature Liquid Lithium Sulfonimide Salts

As mentioned above, one or more of the room-temperature liquid lithium sulfonimide salt compositions of the present disclosure, such as any of the lithium sulfonimide salt compositions described above or made in accordance with the foregoing description, may be used to make an electrolyte for an electrochemical device, among other things. Such electrolytes can be made using any of a variety of methods, such as by mixing one or more of the room-temperature liquid lithium sulfonimide salt compositions of the present disclosure with one or more solvents, one or more diluents, and/or one or more additives, which solvents, diluents, and additives may be known in the art, or can simply be the one or more of the room-temperature liquid lithium sulfonimide salt compositions neat.

Figure 2:
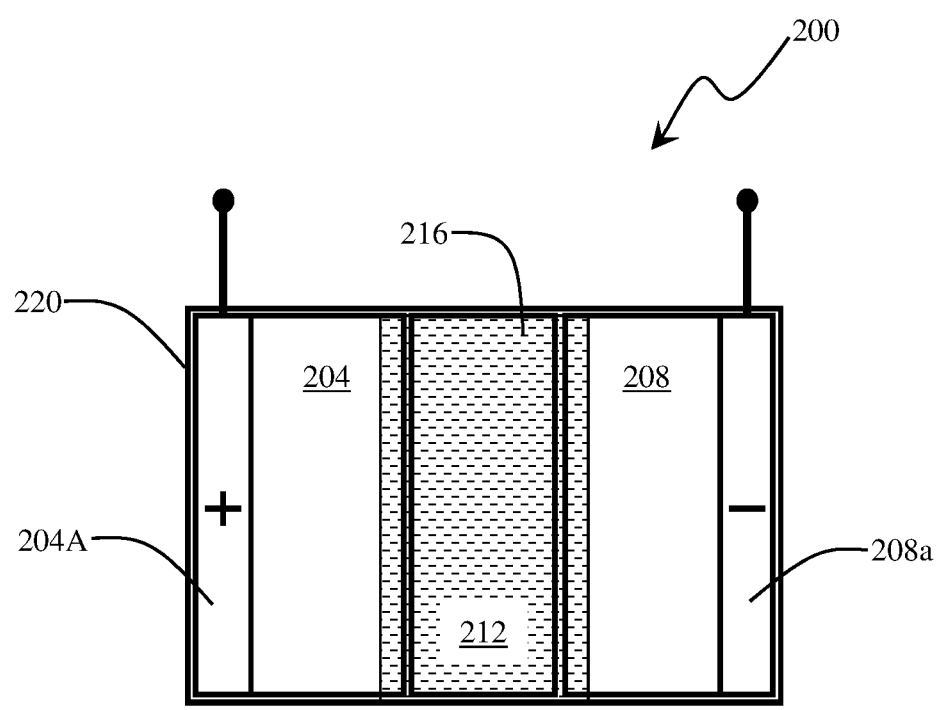
FIG. 2 is a high-level diagram illustrating an electrochemical device made in accordance with aspects of the present disclosure.

FIG. 2 illustrates an electrochemical device 200 made in accordance with aspects of the present disclosure. Those skilled in the art will readily appreciate that the electrochemical device 200 can be, for example, a battery or a supercapacitor. In addition, those skilled in the art will readily understand that FIG. 2 illustrates only some basic functional components of the electrochemical device 200 and that a real-world instantiation of the electrochemical device, such as a secondary battery or a supercapacitor, will typically be embodied using either a wound construction or a stacked construction. Further, those skilled in the art will understand that the electrochemical device 200 will include other components, such as electrical terminals, seal(s), thermal shutdown layer(s), and/or vent(s), among other things, that, for ease of illustration, are not shown in FIG. 2.

In this example, the electrochemical device 200 includes spaced-apart positive and negative electrodes 204, 208, respectively, and a pair of corresponding respective current collectors 204A, 208A. A porous dielectric separator 212 is located between the positive and negative electrodes 204, 208 to electrically separate the positive and negative electrodes but to allow ions of an electrolyte 216 made in accordance with the present disclosure to flow therethrough. The porous dielectric separator 212 and/or one, the other, or both of the positive and negative electrodes 204, 208 is/are impregnated with the electrolyte 216. As described above, a benefit of using a electrolyte of the present disclosure for the electrolyte 216 is that no solvent is needed. This is good for high temperature batteries, for example, such batteries used for drilling, among other things. The electrochemical device 200 includes a container 220 that contains the current collectors 204A, 208A, the positive and negative electrodes 204, 208, the porous dielectric separator 212, and the purified $M_A$FSI electrolyte 216.

As those skilled in the art will understand, depending upon the type and design of the electrochemical device, each of the positive and negative electrodes 204, 208 comprises a suitable material compatible with the ions and other constituents in the electrolyte 216. Each of the current collectors 204A, 208A may be made of any suitable electrically conducting material, such as copper or aluminum, or any combination thereof. The porous dielectric separator 212 may be made of any suitable porous dielectric material, such as a porous polymer, among others. Various battery and supercapacitor constructions that can be used for constructing the electrochemical device 200 of FIG. 2, are known in the art. If any of such known constructions is used, a novelty of electrochemical device 200 lies in the use of a room-temperature liquid lithium sulfonimide salt compositions electrolyte 216 that has not been achieved with conventional methods of making lithium sulfonimide salts and corresponding electrolytes.

In one example, the electrochemical device 200 may be made as follows. The electrolyte 216 may be made by first making one or more room-temperature liquid lithium sulfonimide salt compositions using any of the methods disclosed herein. This/these lithium sulfonimide salt composition(s) may then be used either neat as the electrolyte 216 or to make the electrolyte, for example, by adding one or more solvents, one or more diluents, and/or one or more additives that enhance the performance of the electrochemical device 200. The electrolyte 216 may then be added to the electrochemical device 200, after which the container 220 may be sealed.

In some examples, aspects of the present disclosure may also include a free-solvent-free lithium sulfonimide salt composition that is liquid at room temperature. Such a free-solvent-free lithium sulfonimide salt composition may also include one or more of the following features: consists essentially of at least one lithium sulfonimide salt and at least one ether-based solvent; the at least one lithium sulfonimide salt is selected from the group consisting of lithium bis(fluorosulfonyl)imide (LiFSI), lithium bis(trifluoromethylsulfonyl)imide (LiTFSI), and lithium fluorosulfonyl-(trifluoromethylsulfonyl)imide (LiFTFSI); the at least one ether based solvent is selected from the group consisting of dimethoxyethane, ethoxymethoxyethane, diethoxyethane, dimethoxymethane, diethoxymethane, ethoxymethoxymethane, dioxane, and crown ethers; the at least one lithium sulfonimide salt is LiFSI; the at least one ether-based solvent is diethymethane; the at least one lithium sulfonimide salt is LiTFSI; the at least one ether-based solvent is diethymethane; the at least one lithium sulfonimide salt is LiFTFSI; the at least one ether-based solvent is diethymethane; the at least one lithium sulfonimide salt is LiFSI and LiTFSI; the at least one ether-based solvent is diethymethane; substantially all molecules of the at least one ether-based solvent are coordinated with molecules of the at least one lithium sulfonimide salt; and the at least one ether-based solvent is present in the free-solvent-free lithium sulfonimide salt composition in an amount less than 5% by weight of the free-solvent-free lithium sulfonimide salt composition.

In some further examples, aspects of the present disclosure may also include a method of the present disclosure of making an electrochemical device. The method includes synthesizing a free-solvent-free lithium sulfonimide salt composition using any of the methods recited in any of original claims 1-30 of the present application, as filed, formulating an electrolyte using the free-solvent-free lithium sulfonimide salt composition; providing an electrochemical device structure that includes a positive electrode, a negative electrode spaced from the positive electrode, and a volume that extends between the positive and negative electrodes and, when the electrolyte is present therein allows ions in the electrolyte to move between the positive and negative electrodes; and adding the electrolyte to the volume. Such exemplary method may also include one or more of the following features: the electrochemical device is an electrochemical battery, and the electrochemical device structure further includes a separator located within the volume; the electrochemical battery is a lithium-ion battery; and the electrochemical battery is a lithium-metal battery; the electrochemical device is a supercapacitor.

In some further examples, aspects of the present disclosure may also include a lithium sulfonamide salt composition. The lithium sulfonamide salt composition includes an adduct formed from solvating an anhydrous lithium sulfonimide salt with at least one anhydrous ether-based solvent, wherein the lithium sulfonimide salt composition is substantially free of free solvent and is liquid at room temperature. Such exemplary lithium sulfonamide salt composition may also include one or more of the following features: the anhydrous sulfonimide salt is selected from the group consisting of lithium bis(fluorosulfonyl)imide (LiFSI), lithium bis(trifluoromethylsulfonyl)imide (LiTFSI), and lithium fluorosulfonyl-(trifluoromethylsulfonyl)imide (LiFTFSI); the anhydrous sulfonimide salt is LiFSI; the anhydrous sulfonimide salt is LiTFSI; the anhydrous sulfonimide salt is LiFTFSI; and the at least one anhydrous ether-based solvent is selected from the group consisting of dimethoxyethane, ethoxymethoxyethane, diethoxyethane, dimethoxymethane, diethoxymethane, ethoxymethoxymethane, dioxane, and crown ethers.

In some further examples, aspects of the present disclosure may also include an electrochemical device. The device includes a positive electrode; a negative electrode spaced from the positive electrode; a porous dielectric separator located between the positive and negative electrodes; and an electrolyte contained within at least the porous dielectric separator, the electrolyte made using any of the free-solvent-free lithium sulfonimide salt composition of the present disclosure, for example, any one of the compositions described in paragraphs [0054] and [0056] above.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

What is claimed is:

1. A method of synthesizing a free-solvent-free lithium sulfonimide salt composition, the method comprising:
    contacting at least one anhydrous lithium sulfonimide salt with at least one anhydrous ether-based solvent under inert conditions to create a solution containing the at least one anhydrous lithium sulfonimide salt, wherein the at least one anhydrous ether-based solvent in the solution comprises a free portion that is not adducted to the at least one anhydrous lithium sulfonimide salt; and
    removing substantially all of the free portion of the at least one anhydrous ether-based solvent in the solution so that the free-solvent-free lithium sulfonimide salt composition remains, wherein the free-solvent-free lithium sulfonimide salt composition is liquid at room temperature, and the free-solvent-free lithium sulfonamide salt composition contains less than about 0.5% by weight of the at least one anhydrous ether-based solvent.

2. The method of claim 1, wherein the at least one anhydrous lithium sulfonimide salt comprises lithium bis(fluorosulfonyl)imide (LiFSI).

3. The method of claim 2, wherein the at least one anhydrous ether-based solvent is dimethoxyethane.

4. The method of claim 1, wherein removing substantially all of a free portion of the at least one anhydrous ether-based solvent is performed at a pressure of 100 Torr or less.

5. The method of claim 4, wherein removing substantially all of a free portion of the at least one anhydrous ether-based solvent is performed at a temperature in a range of about −78° C. to about 100° C.

6. The method of claim 5, further comprising, while contacting the at least one anhydrous lithium sulfonimide salt with a minimum amount of at least one anhydrous ether-based solvent, stirring the solution and cooling the solution.

7. The method of claim 6, wherein the minimum amount is in a range of about 20% by weight of the solution to about 22% by weight of the solution.

8. The method of claim 7, wherein the free-solvent-free lithium sulfonimide salt composition is an LiFSI composition that is a clear colorless liquid at room temperature.

9. The method of claim 1, wherein the at least one anhydrous lithium sulfonimide salt comprises lithium fluorosulfonyl(trifluoromethylsulfonyl)imide (LiFTFSI).

10. The method of claim 9, wherein the at least one anhydrous ether-based solvent is dimethoxyethane.

11. The method of claim 9, wherein removing substantially all of a free portion of the at least one anhydrous ether-based solvent is performed at a pressure of 100 Torr or less.

12. The method of claim 11, wherein removing substantially all of a free portion of the at least one anhydrous ether-based solvent is performed at a temperature in a range of about −78° C. to about 100° C.

13. The method of claim 1, further comprising, while contacting the at least one anhydrous lithium sulfonimide salt with a minimum amount of at least one anhydrous ether-based solvent, stirring the solution and cooling the solution.

14. The method of claim 13, wherein the free-solvent-free lithium sulfonimide salt composition is an LiFTFSI composition that is a clear colorless liquid at room temperature.

15. The method of claim 1, wherein the anhydrous lithium sulfonimide salt comprises lithium bis(trifluoromethylsulfonyl)imide (LiTF SI).

16. The method of claim 15, wherein the at least one anhydrous ether-based solvent consists essentially of diethoxyethane.

17. The method of claim 15, wherein removing substantially all of a free portion of the at least one anhydrous ether-based solvent is performed at a pressure of 100 Torr or less.

18. The method of claim 17, wherein removing substantially all of a free portion of the at least one anhydrous ether-based solvent is performed at a temperature in a range of about −78° C. to about 100° C.

19. The method of claim 18, wherein the free-solvent-free lithium sulfonimide salt composition is an LiTFSI composition that is a clear colorless liquid at room temperature.

20. The method of claim 1, wherein the at least one anhydrous ether-based solvent is selected from the group consisting of dimethoxyethane, ethoxymethoxyethane, diethoxyethane, dimethoxymethane, diethoxymethane, ethoxymethoxymethane, dioxane, and crown ethers.

21. The method of claim 20, wherein each of the at least one anhydrous ether-based solvent has a water content of about 2,000 parts-per-million or less.

22. The method of claim 20, wherein the at least one anhydrous lithium sulfonimide salt is from the group consisting of lithium bis(fluorosulfonyl)imide (LiFSI), lithium bis(trifluoromethylsulfonyl)imide (LiTFSI), and lithium fluorosulfonyl-(trifluoromethylsulfonyl)imide (LiFTFSI).

23. The method of claim 1, wherein removing substantially all of a free portion of the at least one anhydrous ether-based solvent is performed at a pressure of about 1 Torr or less.

24. The method of claim 23, wherein removing solvent is performed at a temperature in a range of about −78° C. to about 100° C.

25. The method of claim 24, further comprising, while contacting the at least one anhydrous lithium sulfonimide salt with a minimum amount of at least one anhydrous ether-based solvent, stirring the solution and cooling the solution.

26. The method of claim 25, wherein the free-solvent-free lithium sulfonimide salt composition is a clear colorless liquid at room temperature.

27. The method of claim 1, wherein contacting the at least one anhydrous lithium sulfonimide salt with the at least one anhydrous ether-based solvent includes contacting the at least one anhydrous lithium sulfonimide salt with only a minimum amount of the at least one anhydrous ether-based solvent needed to create the solution.

28. The method of claim 27, wherein the minimum amount is in a range of about 20% by weight of the solution to about 22% by weight of the solution.

29. The method of claim 1, wherein the free-solvent-free lithium sulfonimide salt composition contains less than about 0.1% of the at least one anhydrous ether-based solvent.

30. The method of claim 1, wherein the free-solvent-free lithium sulfonimide salt composition consists essentially of an adduct of the at least one lithium sulfonimide salt and the at least one anhydrous ether-based solvent.

\* \* \* \* \*